United States Patent
Jones, Jr. et al.

(10) Patent No.: US 7,343,034 B2
(45) Date of Patent: Mar. 11, 2008

(54) METHOD OF INSPECTING THREADED FASTENERS AND A SYSTEM THEREFOR

(75) Inventors: James D. Jones, Jr., Barrington, IL (US); Daniel A. Dechant, Darlington, WI (US)

(73) Assignee: Illinois Tool Works Inc, Glenview, IL (US)

( * ) Notice: Subject to any disclaimer, the term of this patent is extended or adjusted under 35 U.S.C. 154(b) by 1045 days.

(21) Appl. No.: 10/737,699

(22) Filed: Dec. 16, 2003

(65) Prior Publication Data

US 2005/0094868 A1 May 5, 2005

Related U.S. Application Data

(63) Continuation-in-part of application No. 10/698,045, filed on Oct. 30, 2003, now Pat. No. 7,245,759.

(51) Int. Cl.
*G06K 9/00* (2006.01)

(52) U.S. Cl. .............. 382/152; 382/141; 382/149; 382/151

(58) Field of Classification Search ............. 382/152, 382/141, 149, 151
See application file for complete search history.

(56) References Cited

U.S. PATENT DOCUMENTS 6,055,329 A * 4/2000 Mufti .................. 382/152

\* cited by examiner

*Primary Examiner*—Matthew C. Bella
*Assistant Examiner*—Mike Rahmjoo
(74) *Attorney, Agent, or Firm*—Mark W. Croll; Paul F. Donovan (57) ABSTRACT

The present invention relates to novel automated inspection systems and related methods of use. In particular, the present invention provides an automated threaded fastener inspection system, and related methods of use. Furthermore, the present invention provides systems and methods for identifying damaged threaded fasteners prior to industrial use.

21 Claims, 9 Drawing Sheets

METHOD OF INSPECTING THREADED FASTENERS AND A SYSTEM THEREFOR

This is a Continuation-In-Part of U.S. patent application Ser. No. 10/698,045, filed Oct. 30, 2003 now U.S. Pat. No. 7,245,759 and entitled Method of Inspecting Threaded Fasteners and a System Therefor.

FIELD OF THE INVENTION

The present invention relates to automated inspection systems and methods of inspection. In particular, the present invention provides a threaded fastener inspection system, and related inspection methods. Furthermore, the present invention provides systems and methods for identifying damaged threaded fasteners prior to their industrial use.

BACKGROUND

Threaded fasteners are used for many applications and must be transported during manufacture and use. During transit and processing, threaded fasteners may become damaged. For example, within a large batch of threaded fasteners, a small number of threaded fasteners may suffer thread damage as they come into contact with other fasteners or with handling equipment. The use of damaged threaded fasteners can result in a defective and potentially unsafe product.

Damaged threaded fasteners are particularly costly for automobile manufacturers. Assembly of automobile engines relies upon threaded fasteners to seal critical engine components. The use of damaged threaded fasteners can result in an improperly sealed engine that is prone to fluid leaks. Automobile manufacturers and suppliers implement post production inspection equipment to locate defective parts such as threaded fasteners. However, post production removal of fasteners is expensive as the engine may need to be disassembled and reassembled. As such, it is desirable to locate defective fasteners prior to assembly.

One inspection technique currently used is a manual inspection of each threaded fastener prior to its use within part assembly. This technique suffers from many problems. Notably, this technique is very expensive, slow, and suffers from human error.

A second inspection technique currently used involves the use of a camera to photograph the threads of a threaded fastener. One problem with this approach is that the camera is unable to capture the entire thread of the threaded fastener. Only a single profile is generally observed. If a thread defect is oriented away from the photographic range of the camera, it will remain undetected.

Accordingly, what is needed in the art are systems and methods for identifying damaged threaded fasteners prior to incorporation into an assembled product.

SUMMARY

The present invention relates to automated inspection systems and methods of inspection. In particular, the present invention provides a threaded fastener inspection system, and related inspection methods. Furthermore, the present invention provides systems and methods for identifying damaged threaded fasteners prior to their industrial use.

Accordingly, the present invention provides a threaded fastener inspection system. In preferred embodiments the threaded fastener inspection system comprises a conveyor, at least one imaging device, and a computer processor. In some embodiments, the imaging device images threaded fasteners at a plurality of views during rotation of a threaded fastener along the conveyor. In further embodiments, the computer processor interfaces with the imaging device. In further embodiments, the computer processor is programmed to analyze the major and minor diameters of the threaded fastener at said plurality of views and compare said major and minor diameters to predetermined values to detect threaded fastener damage.

In further preferred embodiments, the conveyor comprises a rail and a belt. In some embodiments, a portion of said belt is aligned along the length of the rail so that threaded fasteners are secured between the belt and the rail and so that movement of the belt results in the rotation of a threaded fastener along the rail. In preferred embodiments, the rail is a spring loaded rail.

In other preferred embodiments, the imaging device captures an image of threaded fasteners for each 30 degree rotation a threaded fastener makes as it travels within the range of view of the imaging device. In preferred embodiments, the imaging device is stationary.

In some preferred embodiments, the conveyor further comprises a distal end and a sorter, wherein the sorter is positioned at the distal end of the conveyor and wherein the sorter is activated when the computer processor identifies a defective threaded fastener so that damaged threaded fasteners are sorted from undamaged threaded fasteners. In further embodiments, the sorter is a trapdoor. In even further embodiments, the threaded fasteners identified as damaged are discarded into the sorter. In further preferred embodiments, an illumination device is oriented opposite of the imaging device.

The present invention further provides a method of identifying damaged threaded fasteners, comprising providing threaded fasteners, rotating said threaded fasteners, imaging the threaded fasteners at a plurality of views during the rotation, determining major and minor diameters of the threaded fasteners at the plurality of views, comparing the major and minor diameters to predetermined values to determine if the threaded fasteners are damaged, and sorting damaged threaded fasteners from undamaged threaded fasteners. In further embodiments, the comparing is performed by a computer processor.

In even further embodiments, the threaded fasteners are rotated on a conveyor. In still further embodiments, the imaging is performed by a digital camera. In some embodiments, the at least one imaging device captures an image of the threaded fasteners for each 30 degrees of rotation a threaded fastener undergoes as said threaded fastener travels within the range of view of said at least one imaging device. In further embodiments, six views are captured.

In other preferred embodiments, the present invention provides a threaded fastener inspection system comprising a light source, a light shield, a reflector having a sleeve therein for receiving a threaded fastener having a head, and an imaging device positioned to capture a back-lit image of the threaded fastener head. In further embodiments, the sleeve supports the threaded fastener head over the reflector, and the light shield and the reflector are positioned to direct light from the light source so that the threaded fastener head is back-lit. In further embodiments, the light source comprises a circular array of light emitting diodes. In further embodiments, the circular array of light emitting diodes is positioned over the light shield so that the threaded fastener head is shielded from being substantially directly illuminated by the circular array of light emitting diodes. In other embodiments, the light shield is conical in shape. In preferred embodiments, the reflector is formed from a polymeric material. In further embodiments, the reflector comprises Delran.

In even further embodiments, the system further comprises a plurality of said reflectors. In further embodiments, the plurality of reflectors are arranged in a rotating tray. In preferred embodiments, the light source and the light shield are movably mounted so that the light shield and the light source can be raised and lowered over the reflector. In further embodiments, the imaging device is a digital camera. In even further embodiments, the imaging device comprises a processor. In preferred embodiments, the processor is configured to analyze images captured by the digital camera. In yet further embodiments, the system further comprises a thread damage inspection system.

The present invention further provides a method of identifying damaged threaded fasteners comprising providing at least one threaded fastener having a head and an imaging device, back-lighting said head of the threaded fastener, producing a back-lit image of the head of the threaded fastener, and analyzing the back-lit image of the head of the threaded fastener to detect damaged threaded fastener heads. In further embodiments, the method further comprises the step of sorting damaged threaded fastener heads from non-damaged threaded fastener heads. In preferred embodiments, the imaging device is a digital camera. In further preferred embodiments, the imaging device comprises a processor. In preferred embodiments, the processor is configured to identify the center of the head of the threaded fastener, measure a plurality of radii from the center, and compare the measurements to pre-determined values to identify damaged threaded fastener heads. In further embodiments, the processor is further configured to compare an overlapping series of averaged radii measurements to pre-determined values to identify damaged threaded fastener heads.

Other features and advantages of the invention will become apparent to those skilled in the art upon review of the following detailed description, claims and drawings in which like numerals are used to designate like features.

Before the embodiments of the invention are explained in detail, it is to be understood that the invention is not limited in its application to the details of construction and the arrangement of the components set forth in the following description or illustrated in the drawings. The invention is capable of other embodiments and of being practiced or being carried out in various ways. Also, it is to be understood that the phraseology and terminology used herein are for the purpose of description and should not be regarded as limiting. The use of "including" and "comprising" and variations thereof is meant to encompass the items listed thereafter and equivalents thereof as well as additional items and equivalents thereof.

DETAILED DESCRIPTION

The present invention provides inspection systems and methods. The illustrated and preferred embodiments discuss these techniques in the context of threaded fastener inspection systems and methods. However, it should be appreciated that the invention is applicable for use in other inspection applications.

The threaded fastener inspection systems and methods of the present invention have numerous advantages over previous prior art devices including, but not limited to, a faster and more precise approach toward assessing threaded fastener damage. FIGS. 1-8 show various preferred embodiments of the threaded fastener inspection systems and methods of the present invention. The present invention is not limited to these particular embodiments.

Threaded Fastener Inspection Systems and Methods

In some embodiments, the present invention provides systems and methods for detecting thread damage within threaded fasteners. Threaded fasteners refer to hardware agents comprising a threaded face and a head. Examples include, but are not limited to, threaded workpieces, nuts, screws, set screws, grub screws, threaded bolts, and the like.

Figure 1A:
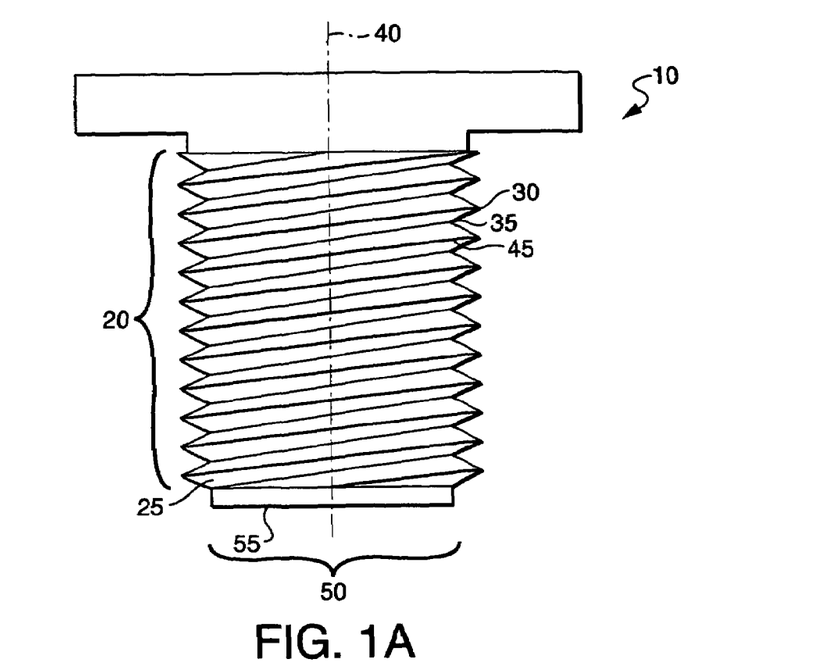
FIG. 1A illustrates an undamaged threaded fastener and FIG. 1B illustrates a damaged threaded fastener.
Figure 1B:
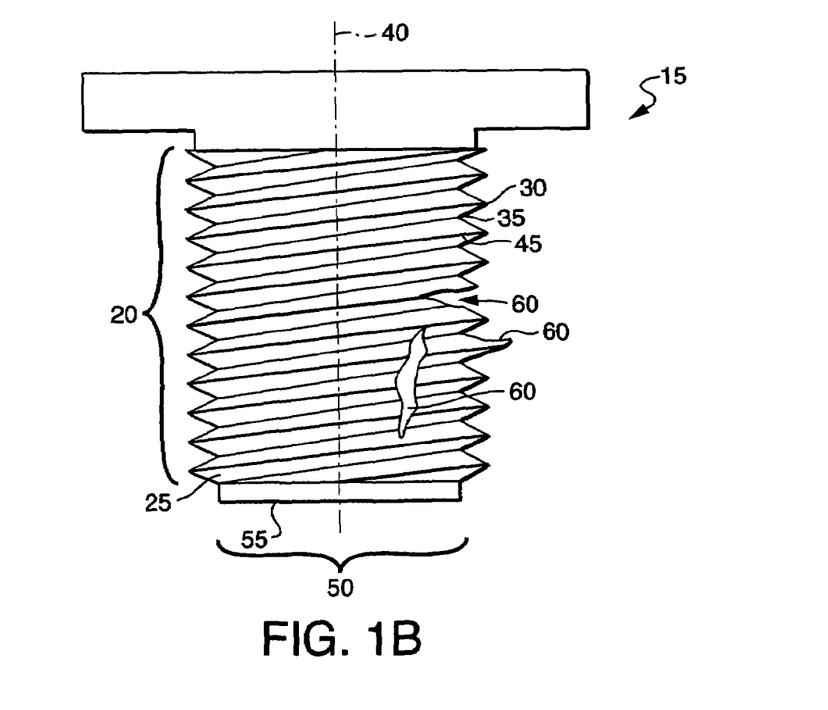

FIG. 1 generally illustrates an undamaged threaded fastener 10 and a damaged threaded fastener 15. A threaded fastener thread face generally comprises a continuous helical ridge 20 formed on the inside (nut) or outside (screw) of a cylinder 25. The apex of the ridge 20 is called the crest 30. Between each crest is a space, called the root 35. Threads are set at an angle to the axis 40 of the bolt or nut. This slope is called the helix angle 45. The helix angle 45 must be sloped, either to the right (for right-hand threaded screws) or the left (for left-hand threaded screws). The threads on a threaded fastener further comprise a major diameter 50 and a minor diameter 55. The major diameter 60 refers to the outside diameter of the thread face and is measured from the outer edge of the crest 30. The minor diameter 55 refers to the inside diameter of the thread face and is measured from the outer edge of the root 35. An undamaged threaded fastener 10 has predetermined or default undamaged major diameter 50 and minor diameter 55 distances. A threaded fastener with damaged threads will have major diameter 50 and minor diameter 55 distances inconsistent with the default undamaged major diameter 50 and minor diameter 55 distances. Referring to FIG. 1, the damaged threaded fastener 55 has a blemish 60 (e.g., a nick or a strip in the thread face) within the thread face. The blemish 60 results in a major diameter 50 distance inconsistent with the undamaged threaded fastener 10 major diameter 50 distance.

The present invention provides systems and methods wherein threaded fasteners are rotatably transported during inspection. Rotatable transport of a threaded fastener refers to rotation of the threaded face along a surface (e.g., rail) resulting in the movement of the threaded fastener along the surface. The thread face may be rotated clockwise or counterclockwise depending on the desired direction of transport. Rotatable transport of a threaded fastener is not limited to a particular speed of transport. In addition, a threaded fastener may be rotatably transported such that the threaded fastener is positioned above, below, or along the direction of transport.

Figure 2:
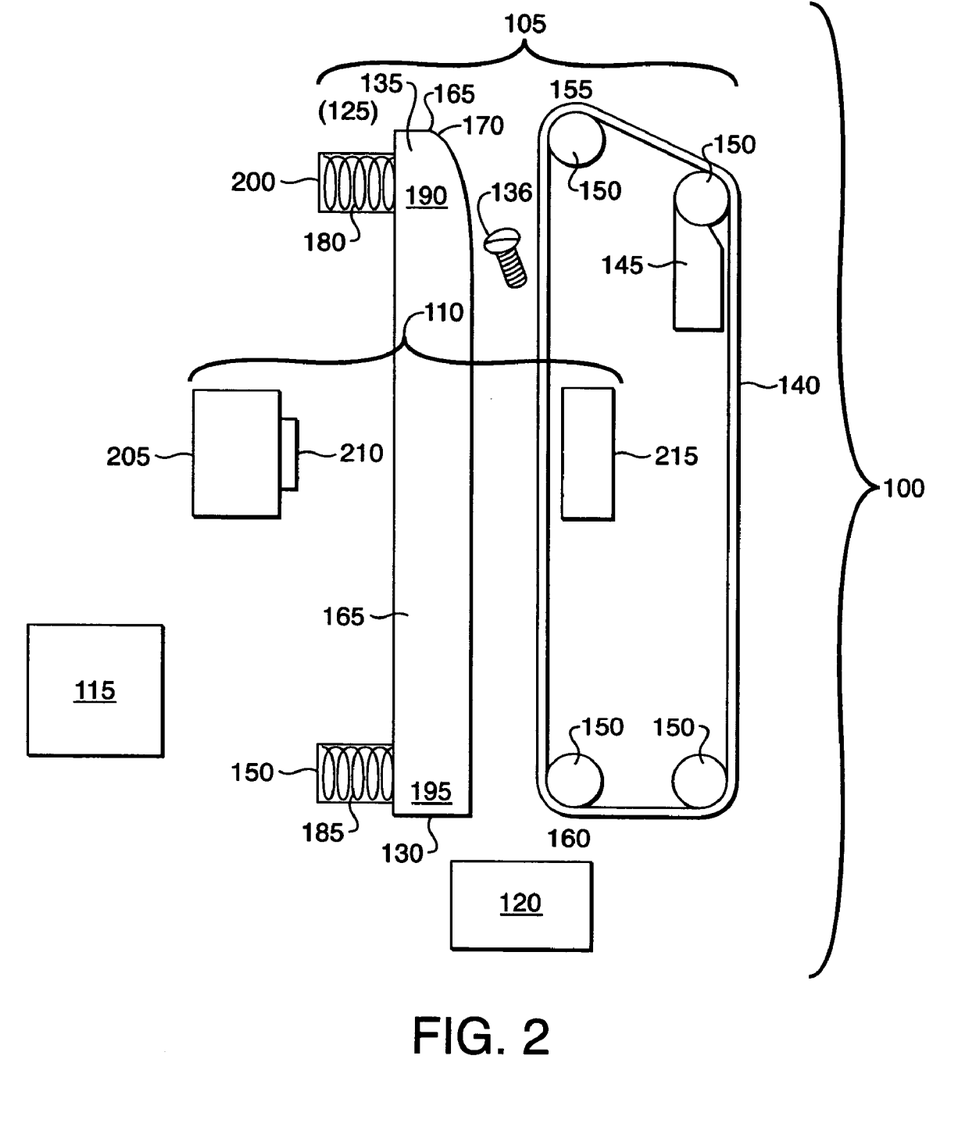
FIG. 2 illustrates a threaded fastener thread damage inspection system.

FIG. 2 illustrates an inspection system 100 of the present invention. In preferred embodiments, the inspection system 100 comprises a conveyor 105, an inspection area 110, a computer processor 115, and a sorter 120.

The conveyor 105 of the present invention rotatably transports threaded fasteners. A conveyor 105 may be driven automatically or manually. In preferred embodiments, the conveyor 105 is driven by an electric motor 145. In some embodiments, the conveyor 105 is positioned at an incline from the conveyor proximal end 125 to the conveyor distal end 130. The conveyor 105 may operate at any desired speed of transport. The conveyor 105 is not limited to a particular length. In preferred embodiments, the conveyor 105 comprises a rail 135 and a belt 140.

In preferred embodiments, the rail 135 comprises any type of material (e.g., steel, metal, plastic, wood) or mixture of such materials. The rail 135 is not limited to a particular length or width. In preferred embodiments, the width of the rail 135 is small in comparison to the length of the threaded fastener so that only a small portion of the face of the threaded fastener is obscured by the rail 135.

In preferred embodiments, the rail 135 is a spring loaded rail 175. In some embodiments, the spring loaded rail 175 comprises at least one spring 180 and 185. In some embodiments, the spring 180 is positioned around a cylinder 200. The cylinder 200 can comprise any type of material (e.g., metal, plastic) or any mixture of such materials. The cylinder 200 is not limited by a particular length or width. The springs 180 and 185 may be adjusted to create a desired tension. In preferred embodiments, the spring loaded rail 175 contains two springs 180 and 185. In further embodiments, the two springs 180 and 185 are positioned at the proximal end 190 and the distal end 195 of the spring loaded rail 175. In even further embodiments, the two springs 180 and 185 are positioned across from rollers 150 positioned at the proximal and distal ends of the belt 140.

The belt 140 can preferably comprise any type of material (e.g., rubber, metal, leather, plastic) or mixture of such materials. The belt 140 may be driven automatically or manually. In preferred embodiments, the belt 140 is driven by a motor 145. The belt 140 is not limited to a particular length or width. In preferred embodiments, the belt 140 is approximately ¼ inch thick. In some embodiments, a fixed shape is maintained in the belt 140 through a plurality of rollers 150. In preferred embodiments, rollers 150 are positioned at the belt proximal end 155 and the belt distal end 160 of the belt 140.

In preferred embodiments, threaded fasteners 136 are rotatably transported between the rail 135 and the belt 140. The belt 140 is positioned along the rail 135. A threaded fastener 136 enters the conveyor 105 at the proximal end 165 of the rail 135. In some embodiments, the proximal end 165 of the rail 135 is rounded 170 to facilitate the entrance of threaded fastener 136 between the rail 135 and the belt 140.

Figure 3:
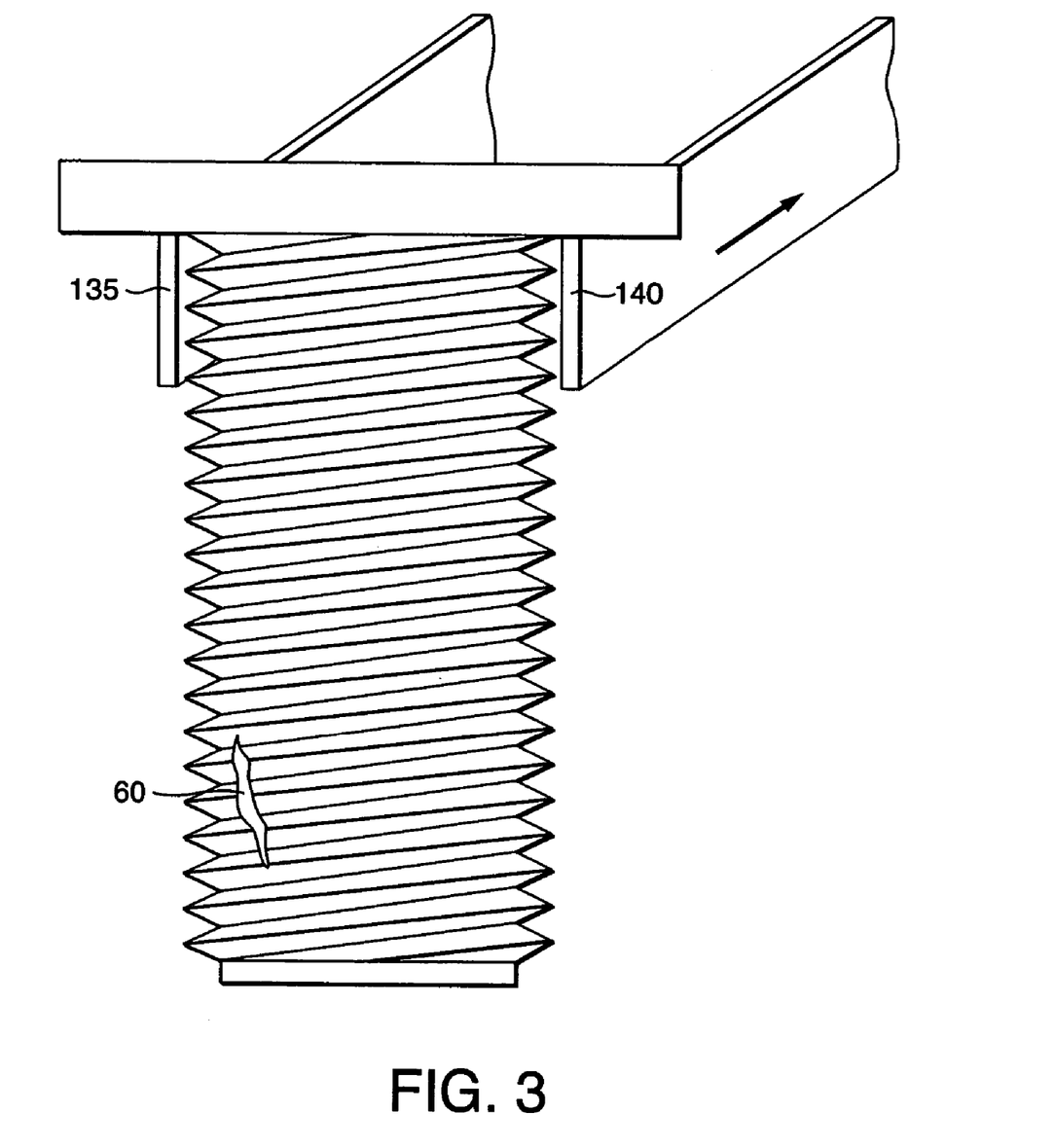
FIG. 3 illustrates a threaded fastener in the threaded fastener thread damage inspection system of FIG. 2.

FIG. 3 illustrates a threaded fastener between the rail 135 and the belt 140. The upper end of the threaded fastener thread face is positioned between the rail 135 and the belt 140. The head of the threaded fastener is positioned above the rail 135 and the belt 140. The movement of the belt 140 results in the threaded fastener transporting along the rail 135. Alternatively, the head of the threaded fastener can ride on a pair of spaced apart rails with the belt 140 being located beneath one of the rails.

Returning to FIG. 2, the inspection area 110 comprises an imaging device 205 and an illumination device 210. The imaging device 205 (e.g., digital camera) may further be positioned anywhere along the length of the rail 135. The imaging device 205 may be held in a stationary position or may be mobile. In preferred embodiments, the imaging device 205 is stationary. The present invention is not limited to any particular type of imaging device 205. Furthermore, the imaging device 205 may be adjusted to accommodate imaging of threaded fasteners of various sizes and shapes.

The inspection area 110 further comprises an illumination device 215 (e.g., light bulb). The illumination device 215 is not limited to any particular strength (e.g., wattage). In some embodiments, the illumination device 215 is positioned beneath the belt 140 so that a threaded fastener traveling along the conveyor 105 is back-lit. The illumination device 215 is further positioned directly across from the imaging device 205.

Figure 4:
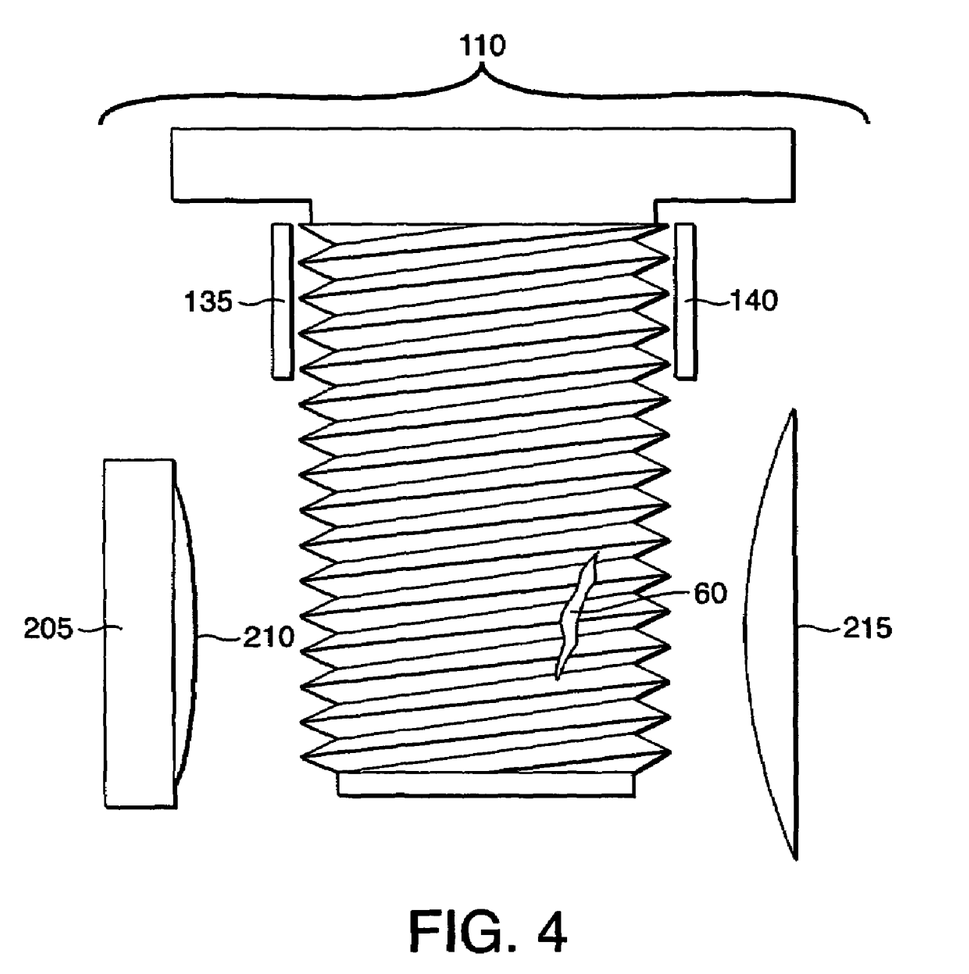
FIG. 4 illustrates the inspection area of the threaded fastener thread damage inspection system.
Figure 5A:
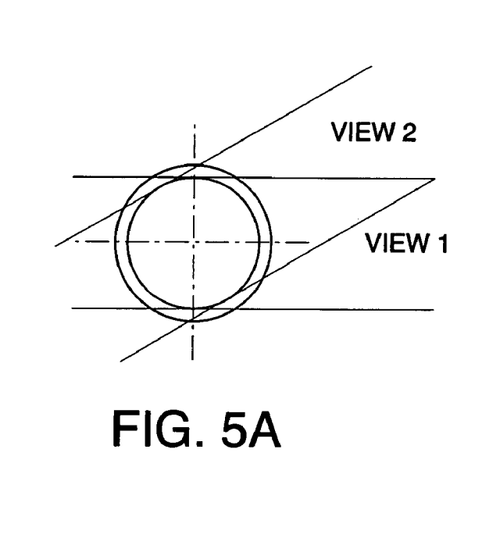
FIG. 5A-F illustrate the range of view of an imaging device within the threaded fastener thread damage inspection system.
Figures 5B, 5C:
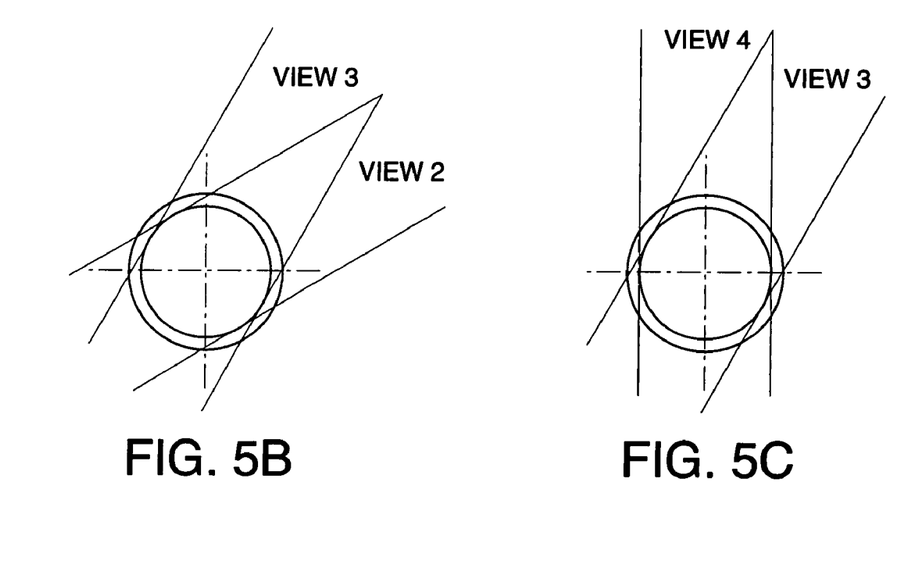
Figure 5D:
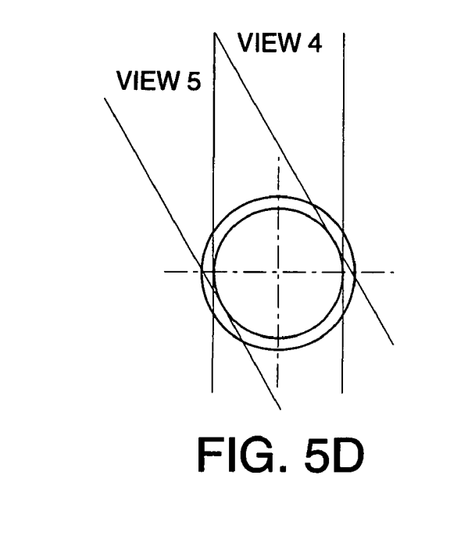
Figure 5E:
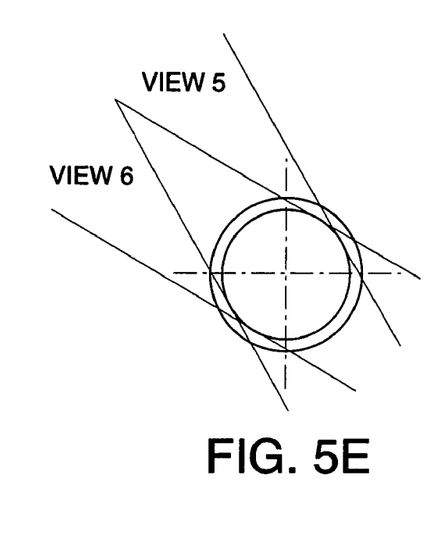
Figure 5F:
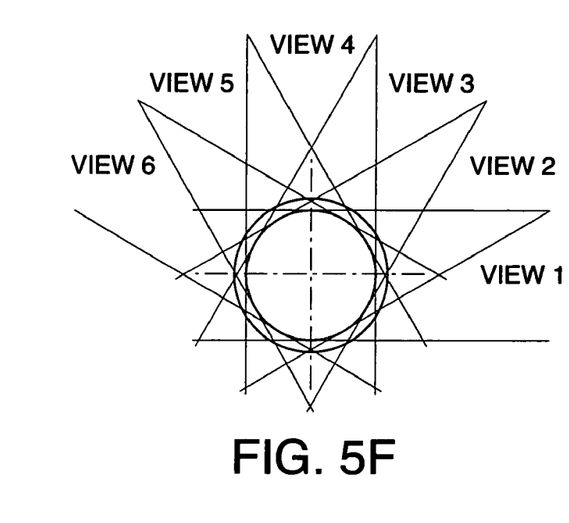

FIG. 4 illustrates a threaded fastener within an inspection area 110. An imaging device 205 (e.g., digital camera) is positioned below the rail 135. In preferred embodiments, the imaging device 205 is positioned so that the upper end of the imaging device lens 210 is positioned in line with the lowest point of the rail 135. As discussed above, a threaded fastener positioned between the rail 135 and belt 140 will have the majority of its threaded face exposed beneath the rail 135 and belt 140. The imaging device lens 210 is further positioned so as to be within view of the entire exposed threaded face of a threaded fastener positioned between the rail 135 and belt 140.

The present invention is configured to image the thread face of a threaded fastener traveling along the rail 135. In preferred embodiments, a rotating threaded fastener passing within the range of view of the imaging device 205 will expose at least half (e.g., 180 degrees) of its face to the imaging device lens 210. It will be recognized that the speed of the motor 145 can be varied to vary the speed of the belt 140 and thus the speed of rotation of the threaded fastener. The imaging device 205 is configured to capture a plurality of images of the thread face of a threaded fastener rotating along the rail 135. In preferred embodiments, the imaging device 205 is programmed according to this speed of rotation so that it can capture an image of the threaded fastener for each 30 degree rotation the threaded makes as it travels within the range of view of the imaging device lens 210. As illustrated in FIG. 5, in preferred embodiments the imaging device 205 captures images of the entire (e.g., 360 degree) face of a rotating object if six images are compiled of the rotating object at six successive 30 degree intervals. In addition, six images of a rotating object taken at six successive 30 degree increments ensures that overlapping profiles of the face of the rotating object are captured.

In preferred embodiments, the imaging device 205 is configured to capture six images of the thread face of a threaded fastener rotating along the rail 135. In further preferred embodiments, the imaging device 205 is configured to capture six images of the thread face of a threaded fastener at six successive 30 degree intervals as the threaded fastener rotates along the rail 135.

In preferred embodiments, the imaging device 205 provides images of the thread face of a threaded fastener to the computer processor 115. The present invention is not limited to any type of computer processor 115. In some embodiments, the computer processor 115 is a part of the imaging device 205, while in other embodiments, the computer processor 115 is interfaced with imaging device 205 via a computer cable. The computer processor 115 is programmed to detect damaged threaded fastener thread faces by analyzing the images obtained from the imaging device 205 and comparing the data obtained from this analysis with a set of predetermined threaded fastener face criteria. According to one aspect of the invention, the inspection system is looking for the absence of light. If light is present during the inspection process, the system recognizes that a flaw or defect may be present in the threaded fastener. According to another aspect of the invention, default major and minor diameters for undamaged fasteners are compared to the imaged major and minor diameters. Threaded fasteners not meeting the predetermined threaded fastener face criteria are sorted via a sorter 120. In preferred embodiments, the sorter 120 is a trapdoor.

II. Threaded Fastener Head Inspection Systems and Methods

Threaded fasteners may be defective or damaged in numerous manners (e.g., cracked heads, unsealed heads, split heads, burrs). The threaded fastener inspection systems of the present invention also include systems for identifying damaged threaded fastener heads.

Threaded fasteners are often coated to provide threaded fasteners with different colors. One method of inspecting threaded fastener heads involves directly illuminating and imaging threaded fastener heads followed by subsequent analysis of the acquired image. Such inspection systems, however, often report false positives and negatives due to varied light reflection caused by various colors of threaded fastener heads. The present invention solves this problem by producing a back-lit image of the threaded fastener head.

Figure 6:
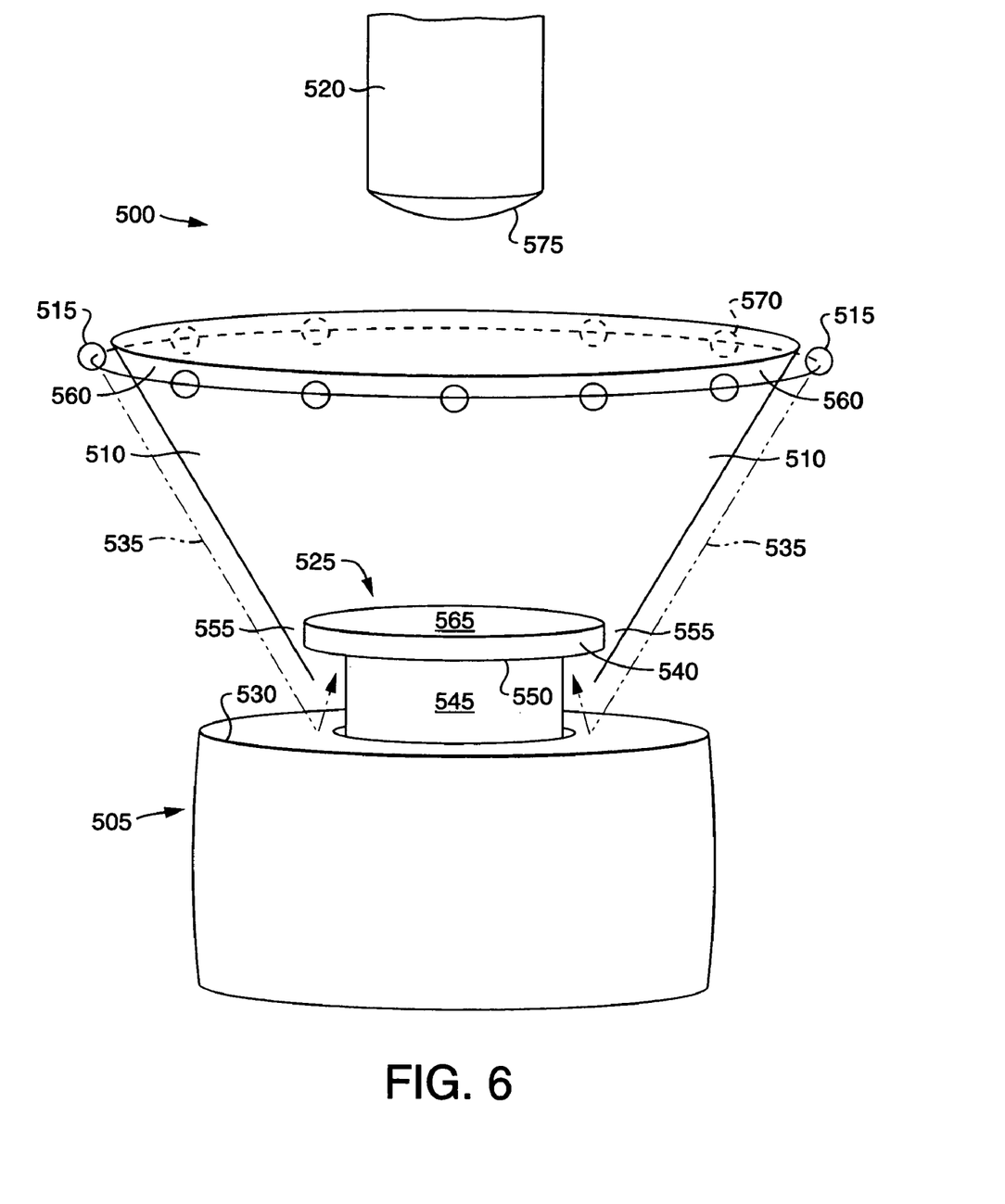
FIG. 6 illustrates a threaded fastener head inspection system.

FIG. 6 illustrates a threaded fastener head inspection system 500 of the present invention. In preferred embodiments, the threaded fastener head inspection system 500 comprises a reflector unit 505, a light shield 510, a light source 515, and an imaging device 520.

Generally, the threaded fastener head inspection systems of the present invention image a threaded fastener head 525 with light reflected from a reflector unit 505. In preferred embodiments, the light emitted from the light source 515 is directed onto a reflector upper surface 530. In such embodiments, the light 535 emitted from the light source 515 is reflected off of the reflector upper surface 530 and directed to the threaded fastener head 525. As such, the light source 515, in conjunction with the reflector unit 505 and light shield 510, generate a back-lit view (e.g., silhouette) of the threaded fastener head 525. In some embodiments, the imaging device 520 is fixedly mounted over the light shield 510 and reflector unit 505. In preferred embodiments, the imaging device 520 images the threaded fastener head 525 illuminated by the light source 515. In some preferred embodiments, described in more detail below, a processor analyzes the image to identify the damaged threaded fastener heads 525.

Still referring to FIG. 6, the reflector unit 505 of the present invention positions the threaded fastener 540 for analysis and reflects light. In some embodiments, the reflector unit 505 comprises a reflector upper surface 530. In some embodiments, the reflector upper surface 530 and reflector unit 505 have an opening therein. In some embodiments, a sleeve 545 is positioned in the opening. In some embodiments, the sleeve 545 is a cylinder into which a threaded fastener 540 can be inserted. In preferred embodiments, the diameter of the sleeve 545 is matched to the threaded portion of the threaded fastener so that when the threaded fastener 540 is inserted into the sleeve 545, the threaded fastener head 525 is supported by the sleeve top lip 550. In preferred embodiments, the entire or at least a substantial portion of the threaded fastener head 525 is exposed on the outside of the sleeve 545 and is thus available for imaging.

In further preferred embodiments, the threaded fastener head inspection systems 500 of the present invention comprise a plurality of reflector units 505. In even further preferred embodiments, the plurality of reflector units 505 are arranged in an indexed rotating tray.

Still referring to FIG. 6, the reflector upper surface 530 serves to reflect light directed onto its surface area. The reflector upper surface 530 is not limited to a particular type of reflective material (e.g., steel, metal, mirror) or mixture of such materials. In preferred embodiments, the reflector unit 505 and reflector upper surface 530 comprises Delran. In other embodiments, the reflector upper surface 530 and the reflector unit 505 comprise different materials. The reflector upper surface 530 is not limited to a particular shape (e.g., oval, circular, square, rectangular). In preferred embodiments, the reflector upper surface 530 is circular. The reflector upper surface 530 is not limited to particular height or width. In preferred embodiments, the width of the reflector upper surface 530 is greater than the width of the threaded fastener head 525.

Still referring to FIG. 6, the light shield 510 comprises a light shield lower portion 555 and a light shield upper portion 560. The light shield lower portion 555 is preferably sized to be the approximate diameter of the threaded fastener head 525. The light shield lower portion 555 is not limited to a particular shape. In preferred embodiments, the shape of the light shield lower portion 555 is consistent with the shape of the threaded fastener head 525 (e.g., generally circular). The light shield lower portion 555 is not limited to a particular width. In preferred embodiments, the width of the light shield lower portion 555 is consistent with the width of the threaded fastener head 525.

The light shield upper portion 560 is not limited to a particular shape (e.g., oval, circular, square, rectangular). In preferred embodiments, the shape of the light shield upper portion 560 is consistent with the configuration of the light source 515. The light shield upper portion 560 is not limited to a particular width. In preferred embodiments, the width of the light shield upper portion 560 is greater than the width of the light shield lower portion 555.

The light shield 510 is preferably sized to fit around a threaded fastener head 525 and prevent the threaded fastener head top 565 from being directly illuminated. The light shield 510 is not limited to a particular type of material (e.g., metal, wood, plastic, mirror) or mixture of such materials. In preferred embodiments, the light shield 510 is aluminum. The shield 510 is not limited to a particular height. In preferred embodiments, the height of the light shield 510 is larger than the height of the threaded fastener head 525. The light shield 510 is not limited to a particular shape. In preferred embodiments, the light shield 510 is conical (e.g., funnel shaped).

Still referring to FIG. 6, the light source 515 serves to illuminate the reflector upper surface 530 to back-light the threaded fastener head 525. The light source 530 is not limited to a particular illumination source (e.g., infra red light source, black light source, regular light bulb). In some embodiments, the light source 515 comprises a plurality of light emitting diodes 570 (LEDs). In preferred embodiments, the LEDs 570 are arranged in a circular array. The present invention is not limited to a particular number (e.g., 1, 2, 3, 4, 8, 16, 100) of LEDs 570. The present invention is not limited in the spacing of the LEDs 570 with respect to the light shield 510. In preferred embodiments, the LEDs 570 are evenly spaced around the light shield 510. The light source 515 is not limited to a particular brightness. In some embodiments, the light source 515 is positioned on the outside of the light shield 510. The light source 515 is not limited to a particular location with respect to the light shield 510. In preferred embodiments, the light source 510 is positioned on the outside of the light shield upper portion 560. In some embodiments, the light source 515 and the light shield 510 are movably mounted so that the light source 515 and the light shield 510 can be moved between raised and lowered positions over the reflector unit 505. In the lowered position (shown), the light shield 510 extends just to or past the threaded fastener head 525 when in a lowered position.

Still referring to FIG. 6, the imaging device 520 images the back-lit threaded fastener head 525. In some embodiments, the imaging device 520 comprises an imaging device lens 575. The present invention is not limited to a particular type of imaging device 520 (e.g., digital camera, manual camera). In preferred embodiments, the imaging device 520 is a digital camera having a CCD chip to capture an image. In further preferred embodiments, the imaging device is a Legend 540 DVT Smart Image Sensor. In further preferred embodiments, the imaging device 520 comprises a processor. The imaging device 520 is not limited to a particular location within the threaded fastener head inspection system 500. In preferred embodiments, the imaging device 520 is located above the light shield 510. The imaging device 520 is not limited in its range of view. In preferred embodiments, the range of view of the imaging device 520 is at least the entire portion of the threaded fastener head 525. In further preferred embodiments, the imaging device 520 height is adjustable to accommodate various threaded fastener head 525 dimensions.

The threaded fastener head inspection system 500 of the present invention generates an image of a threaded fastener head. In preferred embodiments, the image is a digital image. In further preferred embodiments, the digital image comprises an array of pixels that can be used to represent distances (e.g., diameter, radius) across the threaded fastener head image.

Figure 7:
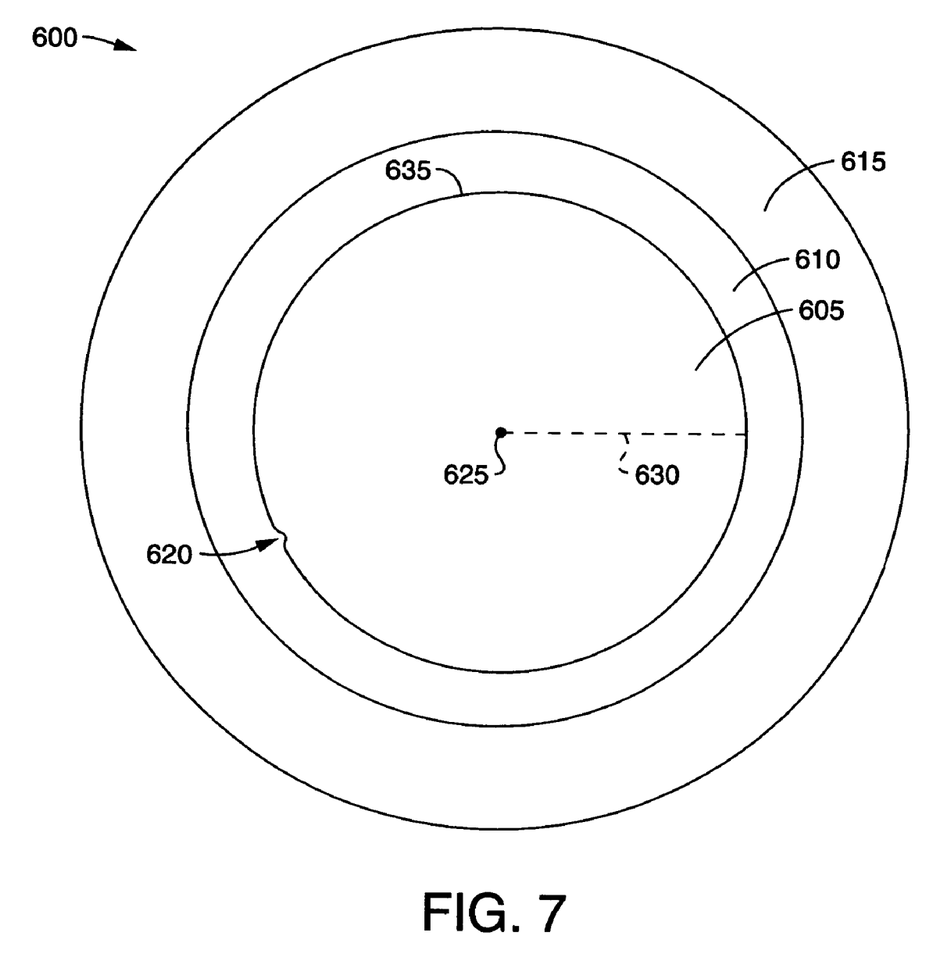
FIG. 7 illustrates a threaded fastener head top image generated with the present invention.

FIG. 7 is a representative depiction of an image 600 of a threaded fastener head obtained from the threaded fastener head inspection systems 500 of the present invention. As illustrated in FIG. 7, the center area is a silhouette image 605 of the threaded fastener head (525, see FIG. 6); the light reflected from the reflector (510, see FIG. 6) is represented as a reflector circle 610 directly around the silhouette image 605; and the outer circle 615 represents a shadow created by the light shield (520, see FIG. 6). The interface 620 between the silhouette image 605 and the reflector circle 610 represents the outer circumference of the threaded fastener head (525, see FIG. 6). FIG. 7 also illustrates a threaded fastener with a blemish 620. FIG. 7 further illustrates various points on the image 600 of the threaded fastener head that are used for subsequent image analysis: the center point 625 and the radius 630.

In some embodiments, the image is analyzed using a processor programmed with instructions for identifying damaged threaded fastener heads. In some preferred embodiments, the processor is located in the imaging device itself, while in other embodiments, the imaging device interfaces with a remote processor in a desktop computer.

The present invention is limited to a particular method of image analysis. In preferred embodiments, the analysis of threaded fastener head images comprises identifying the center point on the threaded fastener head, measuring a plurality of radius distances from the center point 625 to the interface 620, and comparing the measurements to predetermined values or ranges. Of course, it will be recognized that the predetermined values or ranges can differ for various threaded fasteners.

The present invention is not limited to a particular method of identifying a threaded fastener head center point in the image. In preferred embodiments, the processor is programmed with an algorithm for identifying the center point 625 of a threaded fastener head. In some embodiments, the center point 625 is identified by locating the interface 635 between the silhouette image 605 and the reflector circle 610. The processor then analyzes the interface 620 in varying increments and calculates the center of the silhouette image 605. In a preferred embodiment, the increments are 20.2 degree increments.

In some embodiments, the calculated center point is then used as the basis for producing a plurality of threaded fastener head image radius measurements. The present invention is not limited to a particular method of obtaining a plurality of threaded fastener head image radius measurements. In preferred embodiments, the processor is programmed with an algorithm for obtaining threaded fastener head image radius measurements. In preferred embodiments, the processor is programmed to determine the distance (represented by pixels or fractions of pixels) from the threaded fastener center point 625 to the interface 635. The present invention is not limited to a particular number of threaded fastener head image radius measurements. In preferred embodiments, the processor is programmed to determine the radius distance for each 0.5 degree incremental rotation along the interface 635. Accordingly, in some embodiments 720 incremental radius measurements are calculated.

In preferred embodiments, the processor is programmed to determine the difference between radius measurements at each 0.5 degree interval. These measurements are then compared to a predetermined value or range (e.g., the maximum allowable distance between two successive measurements). Threaded fastener heads that produce measurements not in accordance with the predetermined range or value (e.g., threaded fastener heads with blemishes) are designated with a fail condition.

The present invention is not limited in the amount or type of radius distance comparisons. In some preferred embodiments, the processor is programmed to make a series of radius distance comparisons for a particular degree range (e.g., 0.0 degrees to 10.0 degrees, 5.0 degrees to 15.0 degrees, 350.0 degrees to 360.0 degrees, 355.0 degrees to 5.0 degrees, etc.) along the interface. Each degree range (e.g., 10 degrees) along the interface 635 comprises a number of radius measurements (e.g., for radius measurements of 0.5 degrees, a 10 degree range has 20 radius measurements) that are averaged for comparison purposes. By staggering the radius distance comparisons for a particular degree range (e.g., 0.0 degrees to 10.0 degrees, 5.0 degrees to 15.0 degrees, 350.0 degrees to 360.0 degrees, 355.0 degrees to 5.0 degrees, etc.), an overlap in the comparison process along the interface 635 is obtained. The processor is programmed to compare radius distance comparisons for a particular degree range obtained from the image 600 to a predetermined range for the radius distance comparison. Threaded fasteners not falling within the predetermined range are identified as damaged and are assigned a fail condition. In preferred embodiments, threaded fasteners assigned a failed condition are removed from the line by an index shift mechanism.

Figure 8:
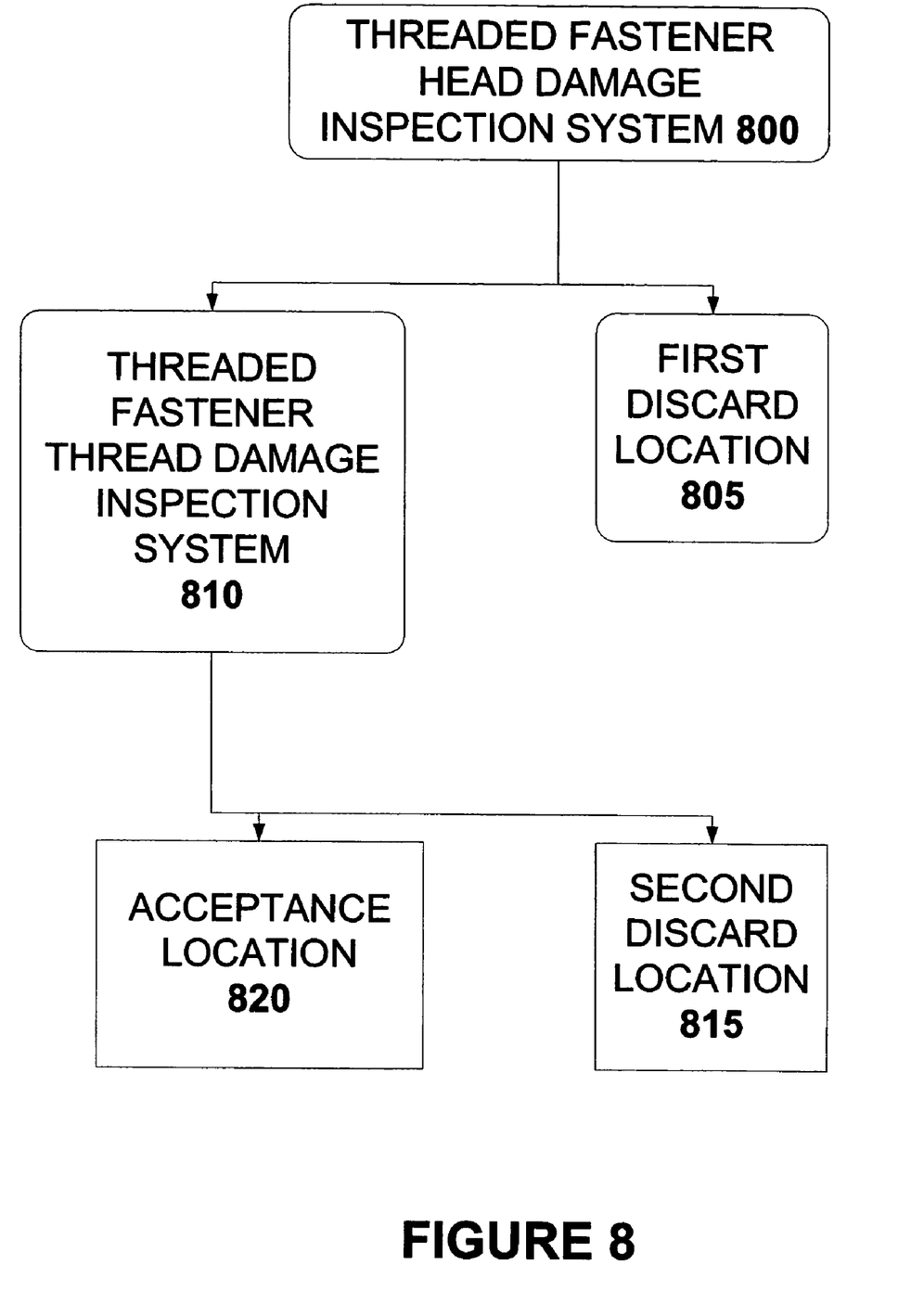
FIG. 8 schematically illustrates a threaded fastener inspection system.

FIG. 8 schematically illustrates a threaded fastener inspection system embodiment for inspecting a plurality of threaded fasteners. In particular, a threaded fastener head damage inspection system 800 interfaces with a first discard location 805 and/or a threaded fastener thread damage inspection system 810. The threaded fastener thread damage inspection system 810 interfaces with either a second discard location 815 or an acceptance location 820. The present invention is not limited to a particular threaded fastener inspection system configuration. Indeed, in some embodiments the present invention provides only a threaded fastener head damage inspection system 800 or only a threaded fastener thread damage inspection system 810. In preferred embodiments, the present invention provides both a threaded fastener head damage inspection system 800 and a threaded fastener thread damage inspection system 810.

All publications and patents mentioned in the above specification are herein incorporated by reference. Variations and modifications of the foregoing are within the scope of the present invention. It is understood that the invention disclosed and defined herein extends to all alternative combinations of two or more of the individual features mentioned or evident from the text and/or drawings. All of these different combinations constitute various alternative aspects of the present invention. The embodiments described herein explain the best modes known for practicing the invention and will enable others skilled in the art to utilize the invention. The claims are to be construed to include alternative embodiments to the extent permitted by the prior art.

Various features of the invention are set forth in the following claims.

The invention claimed is:

1. A threaded fastener inspection system comprising:
   a light source;
   a light shield;
   a reflector having an opening therein for receiving a threaded fastener having a head, wherein said light shield and said reflector are positioned to direct light from said light source so that said threaded fastener head is back-lit;
   an imaging device positioned to produce a back-lit image of said threaded fastener head.

2. The system of claim 1, wherein said reflector comprises a sleeve that receives said threaded fastener, wherein said sleeve supports said threaded fastener head over said reflector.

3. The system of claim 1, wherein said light source comprises a circular array of light emitting diodes.

4. The system of claim 3, wherein said circular array of light emitting diodes is positioned with respect to said light shield so that said threaded fastener head is shielded from being substantially directly illuminated by said circular array of light emitting diodes.

5. The system of claim 1, wherein said light shield is conical in shape.

6. The system of claim 1, wherein said reflector is formed from a polymeric material.

7. The system of claim 1, wherein said reflector comprises Delran.

8. The system of claim 1, further comprising a plurality of said reflectors.

9. The system of claim 8, wherein said plurality of reflectors are arranged in a rotating tray.

10. The system of claim 1, wherein said light source and said light shield are movably mounted so that said light shield and said light source can be raised and lowered over said reflector.

11. The system of claim 1, wherein said imaging device is a digital camera.

12. The system of claim 11, wherein said digital camera comprises a processor.

13. The system of claim 12, wherein said processor is configured to analyze images captured by said digital camera.

14. The system of claim 1, further comprising a thread damage inspection system.

15. A threaded fastener inspection system comprising:
   a light source comprising a circular array of light emitting diodes;
   a light shield;
   a reflector having a sleeve therein for receiving a threaded fastener having a head, wherein said sleeve supports said threaded fastener head over said reflector, wherein said light shield and said reflector are positioned to direct light from said light source so that said threaded fastener head is back-lit, and wherein said circular array of light emitting diodes is positioned over said light shield so that said head of said threaded fastener is shielded from being substantially directly illuminated by said circular array of light emitting diodes;
   an imaging device positioned to capture a back-lit image of said threaded fastener head, wherein said imaging device comprises a processor configured to analyze images captured by said imaging device.

16. A method of identifying damaged threaded fasteners comprising:
   providing at least one threaded fastener having a head and an imaging device;
   back-lighting said head of said threaded fastener;
   obtaining a back-lit image of said head of said threaded fastener; and
   analyzing said back-lit image of said head of said threaded fastener to detect damaged threaded fastener heads.

17. The method of claim 16, further comprising the step of sorting damaged threaded fastener heads from non-damaged threaded fastener heads.

18. The method of claim 16, wherein said imaging device is a digital camera.

19. The method of claim 16, wherein said imaging device comprises a processor.

20. The method of claim 19, wherein said processor is configured to identify the center of said head of said threaded fastener, measure a plurality of radii from said center, and compare said measurements to pre-determined values to identify damaged threaded fastener heads.

21. The method of claim 20, wherein said processor is further configured to compare an overlapping series of averaged radii measurements to pre-determined values to identify damaged threaded fastener heads.

* * * * *